United States Patent [19]

Weimel

[11] Patent Number: 5,303,249
[45] Date of Patent: Apr. 12, 1994

[54] LASER WITH AN ADJUSTMENT DEVICE

[75] Inventor: Erich Weimel, Schnaittach, Fed. Rep. of Germany

[73] Assignee: NWL Laser Technologies GmbH, Schnaittach, Fed. Rep. of Germany

[21] Appl. No.: 920,303

[22] PCT Filed: Jan. 24, 1991

[86] PCT No.: PCT/EP91/00137
§ 371 Date: Aug. 17, 1992
§ 102(e) Date: Aug. 17, 1992

[87] PCT Pub. No.: WO91/12640
PCT Pub. Date: Aug. 22, 1991

[30] Foreign Application Priority Data

Feb. 15, 1990 [CH] Switzerland .................. 489/90

[51] Int. Cl.$^5$ .................................................. H01S 3/00
[52] U.S. Cl. ............................................ 372/33; 372/29; 372/31; 372/32; 372/38
[58] Field of Search .................................. 372/29-33, 372/38

[56] References Cited

U.S. PATENT DOCUMENTS

| 4,692,924 | 9/1987 | Koizumi et al. | 372/30 |
| 5,042,042 | 8/1991 | Hori et al. | 372/32 |
| 5,048,033 | 9/1991 | Donahue et al. | 372/38 |
| 5,151,910 | 9/1992 | Inuyama et al. | 372/38 |

FOREIGN PATENT DOCUMENTS

A3339370  8/1987  Fed. Rep. of Germany.

Primary Examiner—Georgia Y. Epps
Attorney, Agent, or Firm—Brady, O'Boyle & Gates

[57] ABSTRACT

A laser having an adjustment device for varying the output power of the laser. The adjustment device has an adjustment element which is switched in by the operator but cuts out automatically. Using a beam splitter, part of the laser beam is directed on to a light-sensitive element in order to determine the laser power. The values of the selected and instantaneous output power are indicated on the display of a display unit. The adjustment element can be switched in using only one hand and, with the adjustment element switched in, the laser power required can be adjusted using only one hand.

20 Claims, 3 Drawing Sheets

LASER WITH AN ADJUSTMENT DEVICE

The invention relates to a laser with an adjustment device providing a manually operable adjustment element for adjusting the output power of the laser.

BACKGROUND OF THE INVENTION

A laser of this type has been known from DE-OS 3,339,370. The conventional laser emits a pulsed, polarized laser beam, the intensity of which is varied by adjustment of a polarizing cube with an operating knob. After release of the operating knob, a testing pulse is triggered, the energy of this pulse is measured and optionally readjusted. Instead of adjusting the polarizing cube, it is also possible to change the voltage of the laser flash lamp.

SUMMARY OF THE INVENTION

In the use of lasers in medicine or in delicate applications of material machining, their output power must be accurately adjusted and must not be unknowingly altered during operation, in order to avoid accidents or injuries and/or rejects.

The invention is based on the object of avoiding the danger of unintentional adjustment of the laser output power by providing an adjustment device for varying the output power of the laser, which has an adjustment element which is manually coupled into the output power adjusting circuit by the operator, but which automatically decouples from the circuit. Using a beam splitter, part of the laser beam is directed onto a light-sensitive element which determines the output power of the laser beam. The value of the selected output power, which is selected by the adjustment device, and the value of the instantaneous laser output power detected by the light-sensitive element, are indicated on displays of a display unit. The adjustment element can be coupled into the laser power adjustment circuit using only one hand, and with the adjustment element in the coupled-in position, the laser power desired or required can be adjusted using only one hand.

BRIEF DESCRIPTION OF THE DRAWINGS

The laser of the invention is described in greater detail, hereinafter following, with reference to the accompanying drawings, in which.

DESCRIPTION OF THE PREFERRED EMBODIMENTS

Figure 1:
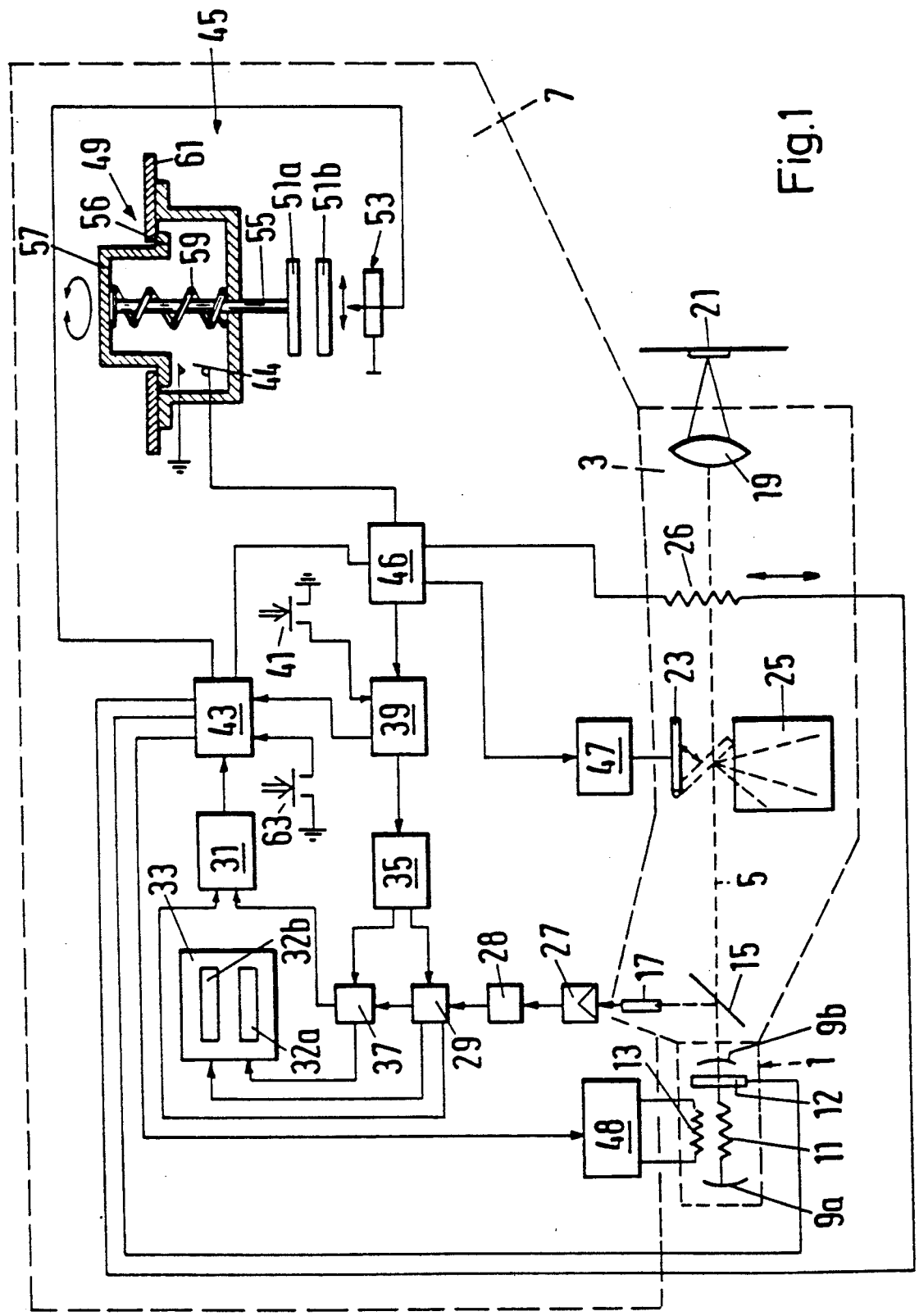
FIG. 1 is a schematic block circuit diagram of the laser of the invention in which the power of the laser beam is varied by the control circuit varying the current from the laser power supply.

The Nd:YAG solid-state laser illustrated in the block circuit diagram of FIG. 1 comprises a laser resonator 1, beam guidance system 3 for the guidance and focusing of the laser beam 5, as well as an electrical control device 7.

The laser resonator 1 has two resonator mirrors 9a and 9b, a neodymium-doped crystal 11 of yttrium-garnet as the active medium, a discharge lamp 13 for stimulation of the crystal 11, and a shutter 12 to cut off the laser beam 5.

The beam guidance system 3 comprises, immediately after exit of the laser beam 5 from the laser resonator 1, a glass plate 15 located at an angle of 45° acting as a partially transparent mirror and directing a small portion of the energy of the laser beam 5 onto a photodiode 17. The remaining, almost entire energy of the laser beam 5 is focused by means of an optical system 19 onto the object 21 to be machined.

A solid, swingable flap 23 is arranged as a deflecting element between the optical system 19 and the partially transparent mirror 15; this flap, in its deflecting position as shown in dashed lines, reflects the laser beam 5 in diffuse fashion into a cavity 25 as the laser beam absorption device; in its rest position (shown in solid lines), the flap 23 is located outside of the laser beam 5. Between the flap 23 and the optical system 19, a so-called safety closure 26 is arranged for blocking the laser beam 5 off from the optical system 19 and thus from the object 21 to be machined.

The photodiode 17 is connected via an amplifier 27 and a signal-processing circuit 28 to an electronic data storage means 29. The storage means 29 is connected to a monitoring circuit 31, a display 33 with two display areas 32a and 32b, as well as to a storage control unit 35 and a further electronic data storage means 37 which latter is likewise connected with the display 33, the monitoring control 31, and the storage control 35. The signal-processing circuit 28 digitizes the signal received by means of the photodiode 17 and amplified by means of the amplifier 27 in correspondence with its intensity and transmits this signal in a continuous clock sequence to the storage means 29 wherein respectively the preceding, stored value is overwritten by a new value of the signal processing circuit 28. The respective value in the storage means 29 is displayed in the display area 32a.

The storage control unit 35 is connected to a logic circuit 39 which latter is connected to an operating key 41, a control circuit 43 and, via a switchover electronic circuit 46, to a contact 44 of an adjustment device 45. The electronic switchover circuit 46 is connected to a switchover driver 47 pivoting the flap 23 in dependence on the position of the contact 44 into the laser beam 5 (deflecting position) and, respectively, out of this beam (rest position). The electronic switchover unit 46 is connected to the control circuit 43 and likewise effects adjustment of the safety switch 26, the latter being swung into or out of the laser beam 5 by an electrical signal from the control circuit 43. A laser power unit 48 (control member for the discharge lamp 13) is connected with the control circuit 43 and receives from the latter control signals for regulating the current through the discharge lamp 13 connected thereto in the laser resonator 1.

The adjustment device 45 has an adjustment element 49, two screen disks 51a and 51b as coupling elements, indicated merely schematically in the block circuit diagram, a rotary potentiometer 53, and the contact 44. The adjusting element 49 is a turning knob 57 attached to an axle 55 and provided with a stop rim 56; this knob is urged by a spring 59 to such extent out of a front plate 61 of a switchboard, not shown, that its stop rim 56 is in contact with the rear face of the front plate 61. The screen disk 51a is attached to the end of the axle 55 in opposition to the turning know 57. The screen disk 51b, acting via an axle, not shown, on the schematically illustrated rotary potentiometer 53, is located in opposition to the screen disk 51a.

The power of the laser beam 5 is varied, as described above, by the current, the so-called pumping light current, through the discharge lamp 13. The power of the laser beam 5 and the current through the discharge lamp 13 are not in a linear relationship to each other. Also, with a fixedly set pumping light current, the laser output power can change, normally decrease, if, inter alia, there is a change in the light emission from the discharge lamp 13 as well as in the optical quality of the laser resonator 1. In order to set the laser power, the rotary knob 57 of the adjustment element 49 of the adjustment device 45 is pressed into the front plate 61 against the bias of the spring 59. Thereby, the contact 44 is closed, the control circuit 43 receives an electrical signal via the electronic switchover unit 46 and the logic circuit 39, whereupon circuit 43 closes the shutter 12 and, as soon as it receives the closing message from the shutter 12, swings the flap 23 into the deflecting position shown in broken lines in the block circuit diagram. Once the flap 23 is in its inwardly swung end position, the control circuit 43 pulls the shutter 12 again out of the laser beam 5. This procedure prevents laser light scattered on edges and surfaces from exiting through the optical system 19.

A portion of the light cut out from the laser beam 5 by means of the partially transparent mirror 15 passes into the photodiode 17. The resultant photocurrent of the photodiode 17 is amplified by the amplifier 27 and averaged by means of the signal-processing circuit 28 over a time period of several hundred milliseconds, digitized, and read into the storage means 29 at a clock frequency in each case corresponding to the reciprocal value of the averaged time; in each case, a value already stored in the memory 29 is written over. The stored value is immediately transmitted to the display area 32a and indicated at that location whereby the display area 32a at all times provides for a reading of the instantaneous value of the laser output power. An average value formation is carried out in order to be able to eliminate short-term fluctuations of the laser output power by a possible so-called spiking or other short-time intensity variations.

The laser beam 5 impinges on the flap 23 and is thereby reflected in diffuse fashion into the cavity 25. Depending on the maximum power of the laser beam 5, the outer walls of the cavity 25 are equipped with cooling ribs or with a water cooling system in order to remove the heat generated by the absorption of the beam 5.

In case the control knob 57 is impressed, as described above, the two screen disks 51a and 51b mesh with each other, the turning knob 57 is mechanically connected to the potentiometer 53, and the resistance value of the potentiometer 53 can be varied by turning the control knob 57. In the impressed condition, the control knob 57 is coupled to the potentiometer 53. The change in the resistance value of the potentiometer 53 has such an effect on the control circuit 43 that a high resistance value yields a high current through the discharge lamp 13, and a low resistance value yields a low current therethrough.

With fine adjustment, a wait of several seconds should advantageously be instituted until a thermal equilibrium has been attained in the laser resonator 1.

Once the desired laser power has been reached, the turning knob 57 is released, the knob being urged outwards by the bias of the spring 59 until it abuts with its stop rim 56 against the rear side of the front plate 61. The turning knob 57 is decoupled from the potentiometer 53. For confirming the thus set value of the laser output power, the confirmation key 41 must be depressed within one second, this key acting via the circuit 39 on the control circuit 43 and the storage control unit 35. Thereby, the adjusted current is maintained in the control circuit 43 at the adjusted value by an internal circuitry. The storage control unit 35 transmits a signal to the memory 29 in order to transfer the value of the laser output power from the storage means 29 into the storage means 37 as the set value, and to display same on the display field 32b.

For starting the laser machining operation, a trigger key 63 connected with the control circuit 43 is pressed. Thereby, the shutter 12 is closed, the flap 23 is flipped back into its rest position shown in solid lines in the block circuit diagram, the shutter 26 is pulled out of the laser beam 5, and, after the shutter 26 has reached its final position outside of the laser beam 5, the shutter 12 is opened again. The laser beam 5 is then focused onto the object 21 by the optical system 19 and machines this object, i.e. with the object 21 being stationary, drills a hole, cuts, heats, exposes, or engraves with the object 21 in motion.

During operation, the laser output power is measured by way of the partially transparent mirror 15 and the photodiode 17. As described above, the display 33 then shows, in the display area 32a, at all times the instantaneous value of the laser output power and, in the display area 32b, the adjustment value of the laser output power. If the instantaneous laser output power exceeds the set value by more than 10%, the current through the discharge lamp 13 is cut out by the monitoring circuit 31 which latter compares both values with each other, by way of the control circuit 43 and the laser power unit 48, in order to avoid rejects, injuries, accidents, etc.

If the set value of the laser output power drops below 10% thereof, then a warning signal will be sounded urging readjustment of the laser power. In case of a more extensive deviation, the current is cut off.

Instead of making the control knob 57 impressible, the adjusting element 49 can also be constructed in such a way that the turning knob must be pulled out for varying the laser output power. The two raster disks can then be fashioned, for example, as gear wheels which mesh only when the turning knob 57 has been pulled out.

Instead of pulling out or impressing the rotary knob 57, the latter can also be equipped with a capacitive sensor responding each time the turning knob is grasped manually. At the instant that the sensor responds, a locking action is then electrically released, and the laser power can be adjusted. Once this rotary knob is released, the knob is again locked electrically. The thus-set power can likewise be confirmed, as described above, by way of the operating key 41.

Instead of pressing the operating key 41, for confirming the thus-adjusted laser power value, after at least one second, it is also possible to choose a different time value in dependence on the operating conditions. Also, confirmation can be entirely omitted if no erroneous actuations of the control knob 57 are possible.

Figure 2:
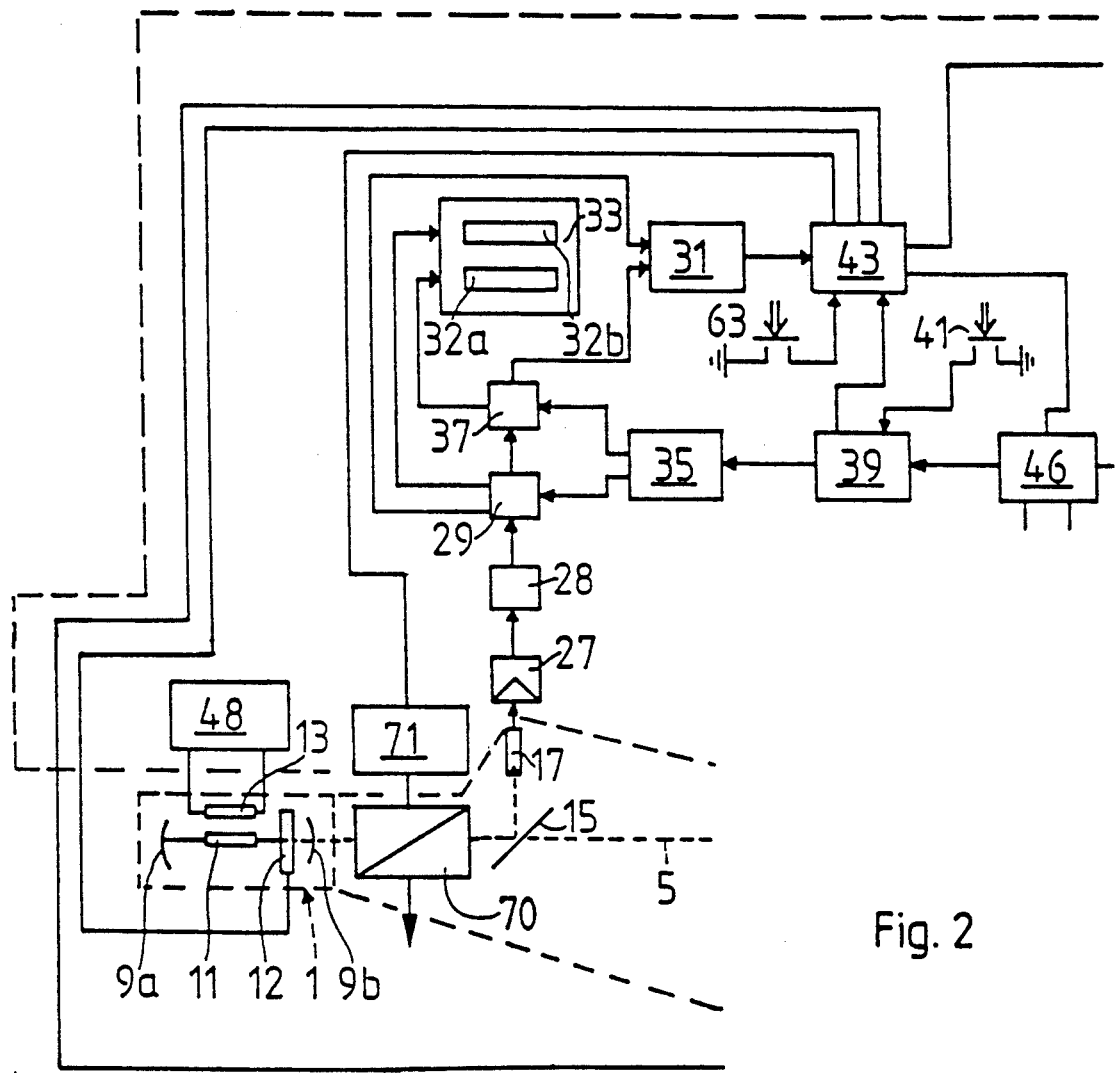
FIG. 2 is a partial schematic block circuit diagram of a modified form of the laser of the invention in which the power of the laser beam is varied by the control circuit adjusting a polarizing beam splitter.
Figure 3:
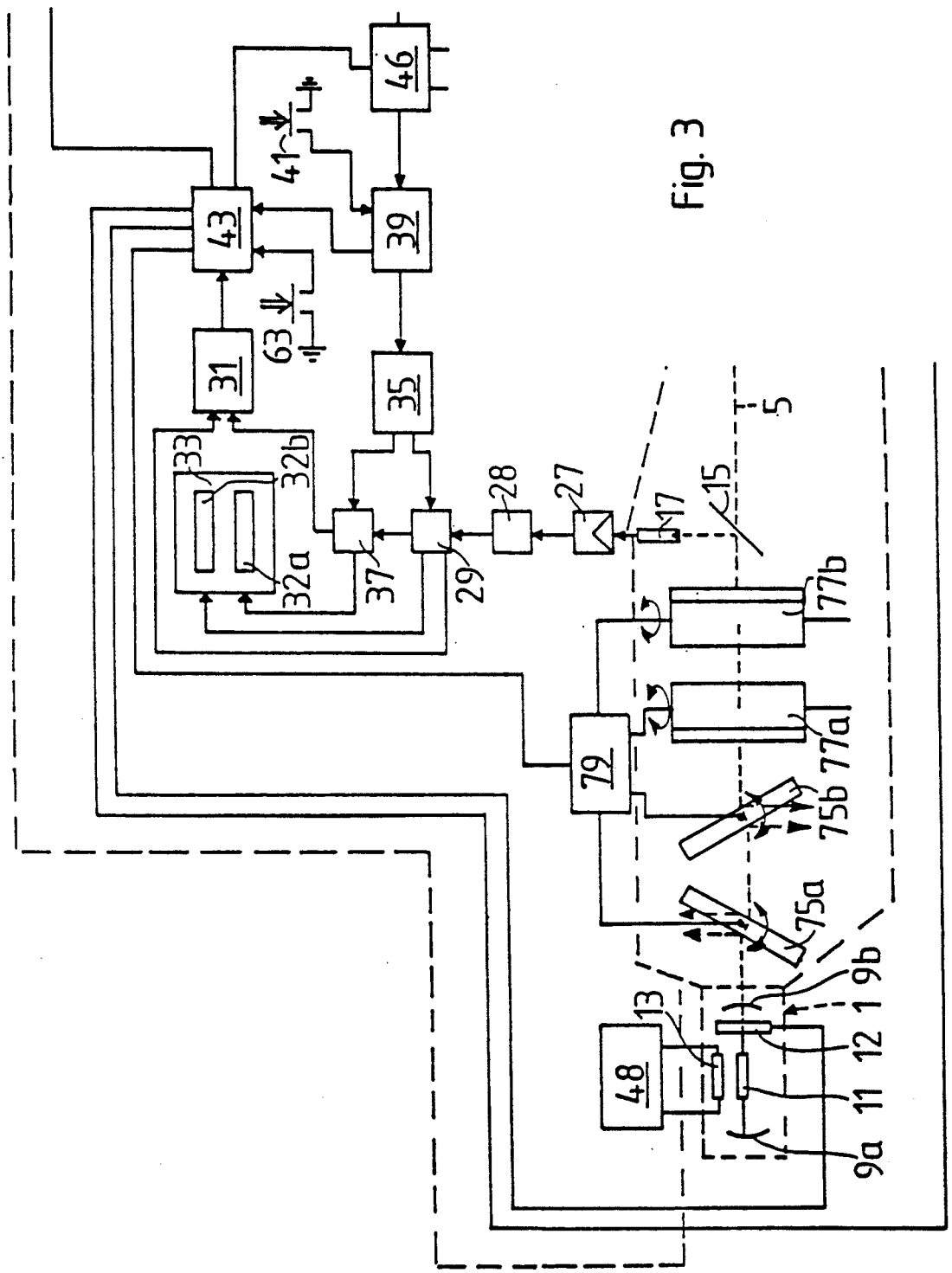
FIG. 3 is a partial schematic block circuit diagram of a further modified form of the invention in which the power of the laser beam is varied by the control circuit adjusting four pivotable glass plates.

Instead of altering the laser power by varying the current through the discharge lamp 13 as shown in the circuit of FIG. 1, the laser power can also be adjusted, insofar as it is polarized, by adjusting 71 a polarizing beam splitter 70 to be arranged between the mirror 9b and the partially transparent mirror 15, as shown in FIG. 2. In place of a polarizing beam splitter 70, it is also possible, as shown in FIG. 3, in case of unpolarized laser output power, to utilize four glass plates 75a, 75b, 77a, 77b provided with an antireflection coating and being pivotable 79 with respect to the laser beam axis 5, wherein the pivoting planes of respectively two plate pairs 75a, 75b, and 77a, 77b are located perpendicularly to each other, and respectively two plates 75a and 75b, 77a and 77b, of a pair are disposed at the same angle with respect to the beam axis 5, but are swung in opposite pivoting directions to avoid spatial displacement of the laser beam 5. The glass plates 75a, 75b, 77a, 77b can be utilized at the same location as the polarizing beam splitter 70.

The Nd:YAG solid-state laser can be a continuous laser with constant output power or with a pulse sequence of constant frequency or repetition frequency. The constant frequency or pulse sequence is produced in the laser resonator 1 by means of an active switching element, not shown, for example an electrooptical switch. Depending on the set intensity of the discharge lamp 13, a pulse sequence is involved which follows the frequency of the optical switch or integral fractions thereof. The higher the intensity of the discharge lamp, the smaller the divisor of the frequency; there are also intensity values wherein the pulse sequence jumps to and fro between two and several frequency values. Since the photocurrent of the photodiode 17 is averaged by the signal-processing circuit 28 over a time period of several hundred milliseconds, the control device 7 can likewise cooperate with this laser, likewise called a continuous laser insofar as the pulse repetition frequency is larger than 500 Hz. Of course, in place of a continuous Nd:YAG laser, other continuous lasers can likewise be employed, such as, for example, a continuous argon laser as well as other gas, ion, excimer lasers, etc.

In the laser according to this invention, the output power cannot be changed by unintentional touching of the turning knob 57 since the latter must first be pressed inwards (or pulled out) and only thereafter can adjustment take place. The confirmation key 41 is provided as an additional safety feature; only by actuating this key will a new power value for changing the output power, set by means of the turning knob 57, be adopted.

I claim:

1. A laser device having a laser resonator (1) for emitting a laser beam with a laser output power, an active element positioned within said laser resonator for generating a laser radiation for said laser beam, said active element connected to be pumped by pumping power of a power supply, measuring means (15, 17) positioned relative to said laser beam for measuring said emitted laser output power, a display device (33) connected to said measuring means (15, 17) and displaying the value of said measured laser output power, an adjustment device (45) having a handling element (57), a coupling element (51a, 51b) and an adjustment element (49) connected for adjusting said pumping power of said power supply, said handling element (57) being manually operable, said coupling element (51a, 51b) cooperatively connected with said adjustment element (49) for movement between a decoupled position and a coupled-in position, and said coupling element moveable manually by said handling element (57) to the coupled-in and a switched-in position for setting said pumping power in correspondence to a desired value of said laser output power, adjusting said pumping power of said power supply by said adjustment element (49) being only possible in the switched-in position of said coupling element (51a, 51b), and means connected with said handling element whereby when released, said coupling element automatically moves from the coupled-in position into the decoupled position wherein adjustment of said adjustment element (49) is ineffective, so that changing of the laser output power by unintentional adjustment of said adjustment element (49) is avoided.

2. A laser device according to claim 1, wherein said laser resonator emits an approximately continuous laser output power or a continuous pulse sequence of pulses having a repetition rate larger than 500 Hz, said laser output power or the height of said pulse being adjustable by said adjustment device (45).

3. A laser device according to claim 1, in which said measuring means (15, 17) having a light-sensitive element (17) and a beam splitter (15), said beam splitter (15) being arranged in the emitted laser output power beam (5) outside said laser resonator (1), said beam splitter (15) cutting out a portion of said laser beam (5), said light-sensitive element (17) being positioned within said portion of said laser beam, and said measuring means (15, 17) being used for the determination of the actual value of said laser output power.

4. A laser device according to claim 3, including a monitoring device (31) connected to said adjustment device (45), to said measuring means (15, 17) and to said laser power supply (48), said monitoring device (31) adapted to compare said desired value set by said adjustment device (45) with the actual value of the laser output power determined by said measuring means (15, 17), said monitoring device (31) operative to turn off said laser output power by said laser power supply (48), when said desired value is exceeded by a predetermined tolerance value of said actual value.

5. A laser device according to claim 4, in which said monitoring device (31) is operative to turn off said laser output power in case said desired value is exceeded in the downward direction by a second tolerance value.

6. A laser device according to claim 3, in which said display device (33) including display element means (32a, 32b) designed for displaying said desired value of the laser output power set with said adjustment device (45) as well as the actual value of the laser output power measured by said measuring means (15, 17).

7. A laser device according to claim 1, in which said adjustment element (49) is constructed so that said coupling element (51a, 51b) cooperatively connected therewith can be moved to the coupled-in position by means of only one hand, and the desired value of the laser output power in the coupled-in position can be varied by said handling element with only said one hand.

8. A laser device according to claim 1, including an absorption device (25) for the laser beam (5) and of the laser output power outside said laser resonator (1), and a laser beam deflection element (23), said deflection element (23) being moveable from a rest position outside of the laser beam (5) into a deflecting position into the path of said laser beam for deflection of said laser beam (5) into said absorption device (25), when said coupling element (51a, 51b) is in the coupled-in position, and said deflection element (23) moveable from said deflecting position back into said rest position, when said coupling element (51a, 51b) moves to the decoupled position.

9. A laser device according to claim 1, including an electronic data storage means (37), and a confirmation key (41); said laser power supply (48) connected in circuit with said adjustment device (45), with said confirmation key (41) and with said electronic data storage means (37);

whereby after actuation of said confirmation key (41) within a predetermined time interval beginning when said coupling element (51a, 51b) is moved to the decoupled position, the value of the laser output power set with said adjustment element (49) in the coupled-in position is transferred into said data storage means (37) and, respectively, is not transferred thereinto in case said confirmation key (41) is not actuated, or is actuated outside of the predetermined time interval; and said laser power supply (48) adjusting said laser output power to the value stored in said data storage means (37) when said coupling element (51a, 51b) moves from the coupled-in position to the decoupled position and, respectively, at the end of the predetermined time interval.

10. A laser device having a laser resonator (1) for emitting a laser beam with a laser output power, measuring means (15, 17) positioned relative to said laser beam for measuring said emitted laser output power, a display device (33) connected to said measuring means (15, 17) and displaying the value of said measured laser output power, transmission means having an adjustable transmissivity for said laser power, said transmission means being positioned in the path of said laser beam (5) between said laser resonator (1) and said measuring means (15, 17), said adjustable transitivity of said transmissivity means being adjustable by displacement means, an adjustment device (45) having a handling element (57), a coupling element (51a, 51b) and an adjustment element (49) cooperatively connected with said displacement means for adjusting the transmissivity of said transmission means for adjusting the laser output power of said laser beam, said handling element (57) being manually operable, said coupling element (51a, 51b) cooperatively connected with said adjustment element (49) for movement between a decoupled position and a coupled-in position, and said coupling element moveable manually by said handling element (57) to the coupled-in and a switched-in position for setting said transmissivity in correspondence to a desired value of said laser output power, adjusting said transmissivity of said transmission means by said adjustment element (49) being only possible in the switched-in position of said coupling element (51a, 51b), and means connected with said handling element whereby when released, said coupling element automatically moves from the coupled-in position into the decoupled position wherein adjustment of said adjustment element (49) is ineffective, so that changing of the laser output power by unintentional adjustment of said adjustment element (49) is avoided.

11. A laser device according to claim 10, in which said transmission means is an adjustable polarizer.

12. A laser device according to claim 11, in which said adjustable polarizer includes four plates transparent for the laser radiation of said laser beam (5), said four plates being coated with a coating effective with said laser radiation, said coating functioning as an antireflection coating when said plates are aligned with said laser beam and said laser beam passes perpendicularly through said plates, each of said four plates having a swivel axis and being pivotable about the respective swivel axis in relation to the propagation direction of said laser beam (5), said four plates being arranged in two-plate pairs, and the swivel axes of one plate pair of said two-plate pairs being connected perpendicular to the swivel axes of the other plate pair of said two-plate pairs.

13. A laser device according to claim 10, wherein said laser resonator emits an approximately continuous laser output power or a continuous pulse sequence of pulses having a repetition rate larger than 500 Hz, said laser output power or the height of said pulse being adjustable by said adjustment device (45).

14. A laser device according to claim 10, in which said measuring means (15, 17) having a light-sensitive element (17) and a beam splitter (15), said beam splitter (15) being arranged in the emitted laser output power beam (5) outside said laser resonator (1), said beam splitter (15) cutting out a portion of said laser beam (5), said light-sensitive element (17) being positioned within said portion of said laser beam, and said measuring means (15, 17) being used for the determination of the actual value of said laser output power.

15. A laser device according to claim 14, including a monitoring device (31) connected to said adjustment device (45), to said measuring means (15, 17) and to said laser power transmission means, said monitoring device (31) adapted to compare said desired value set by said adjustment device (45) with the actual value of the laser output power determined by said measuring means (15, 17), said monitoring device (31) operative to turn off said laser output power by said transmission means, when said desired value is exceeded by a predetermined tolerance value of said actual value.

16. A laser device according to claim 15, in which said monitoring device (31) is operative to turn off said laser output power in case said desired value is exceeded in the downward direction by a second tolerance value.

17. A laser device according to claim 14, in which said display device (33) including display element means (32a, 32b) designed for displaying said desired value of the laser output power set with said adjustment device (45) as well as the actual value of the laser output power measured by said measuring means (15, 17).

18. A laser device according to claim 10, in which said adjustment element (49) is constructed so that said coupling element (51a, 51b) cooperatively connected therewith can be moved to the coupled-in position by means of only one hand, and the desired value of the laser output power in the coupled-in position can be varied by said handling element with only said one hand.

19. A laser device according to claim 10, including an absorption device (25) for the laser beam (5) and of the laser output power outside said laser resonator (1), and a laser beam defection element (23), said deflection element (23) being moveable from a rest position outside of the laser beam (5) into a deflecting position into the path of said laser beam for deflection of said laser beam (5) into said absorption device (25), when said coupling element (51a, 51b) is in the coupled-in position, and said deflection element (23) moveable from said deflecting position back into said rest position, when said coupling element (51a, 51b) moves to the decoupled position.

20. A laser device according to claim 10, including an electronic data storage means (37), and a confirmation key (41);

said laser power transmission means operatively connected in circuit with said adjustment device (45), with said confirmation key (41) and with said electronic data storage means (37);

whereby after actuation of said confirmation key (41) within a predetermined time interval beginning when said coupling element (51a, 51b) is moved to the decoupled position, the value of the laser output power set with said adjustment element (49) in the coupled-in position is transferred into said data storage means (37) and, respectively, is not transferred thereinto in case said confirmation key (41) is not actuated, or is actuated outside of the predetermined time interval; and said laser power transmission means adjusting said laser output power to the value stored in said data storage means (37) when said coupling element (51a, 51b) moves from the coupled-in position to the decoupled position and, respectively, at the end of the predetermined time interval.

* * * * *